United States Patent
Hindley

(10) Patent No.: US 10,278,907 B2
(45) Date of Patent: May 7, 2019

(54) HAIR CARE FORMULATION

(71) Applicant: Croda International PLC, East Yorkshire (GB)

(72) Inventor: Michael Christopher Hindley, East Yorkshire (GB)

(73) Assignee: CRODA INTERNATIONAL PLC, East Yorkshire (GB)

( * ) Notice: Subject to any disclaimer, the term of this patent is extended or adjusted under 35 U.S.C. 154(b) by 0 days.

(21) Appl. No.: 15/574,890

(22) PCT Filed: May 19, 2016

(86) PCT No.: PCT/GB2016/051442
§ 371 (c)(1),
(2) Date: Nov. 17, 2017

(87) PCT Pub. No.: WO2016/189276
PCT Pub. Date: Dec. 1, 2016

(65) Prior Publication Data
US 2018/0161258 A1    Jun. 14, 2018

(30) Foreign Application Priority Data
May 26, 2015    (GB) .................................. 1508971.7

(51) Int. Cl.
*A61Q 5/12*    (2006.01)
*A61K 8/37*    (2006.01)
*A61K 8/362*    (2006.01)

(52) U.S. Cl.
CPC ................ *A61K 8/37* (2013.01); *A61K 8/362* (2013.01); *A61Q 5/12* (2013.01); *A61K 2800/34* (2013.01)

(58) Field of Classification Search
CPC ... A61Q 5/02; A61Q 5/12; A61K 8/37; A61K 2800/34; A61K 8/362
See application file for complete search history.

(56) References Cited

U.S. PATENT DOCUMENTS

| | | | | |
|---|---|---|---|---|
| 5,286,397 A | * | 2/1994 | Schmid | C10M 105/36 508/496 |
| 8,158,680 B2 | | 4/2012 | Ansmann et al. | |
| 2002/0155962 A1 | * | 10/2002 | Cincotta | A61K 8/8182 510/119 |
| 2004/0042988 A1 | * | 3/2004 | Raney | A61K 8/342 424/70.1 |
| 2005/0255067 A1 | * | 11/2005 | Leighton | A61K 8/732 424/70.2 |
| 2007/0207222 A1 | | 9/2007 | Yu et al. | |

FOREIGN PATENT DOCUMENTS

| | | |
|---|---|---|
| DE | 4313948 A1 | 11/1994 |
| EP | 1985281 A1 | 10/2008 |
| FR | 2943243 A1 | 9/2010 |

OTHER PUBLICATIONS

International Search Report and Written Opinion for International Application No. PCT/GB2016/051442, dated Jul. 6, 2016—11 Pages.

* cited by examiner

*Primary Examiner* — Johann R Richter
*Assistant Examiner* — Danielle Sullivan
(74) *Attorney, Agent, or Firm* — RatnerPrestia

(57) ABSTRACT

A hair care formulation comprises a diester of a C8-C26 Guerbet alcohol and a C4-C40 dicarboxylic acid. The diester can function as an active ingredient, particularly as a conditioning agent, especially on dry hair. Silicone-free hair care compositions can be produced with effective conditioning properties on both wet and dry hair.

15 Claims, No Drawings

HAIR CARE FORMULATION

CROSS REFERENCE TO RELATED APPLICATIONS

This application is the National Stage filing of International Appln. No. PCT/GB2016/051442, filed May 19, 2016, and claims priority of GB Application No. 1508971.7, filed May 26, 2015, the entirety of which applications is incorporated herein by reference for all purposes.

FIELD OF INVENTION

The present invention relates to a hair care formulation, more particularly a hair conditioning formulation, and use thereof to achieve a conditioning effect on dry hair.

BACKGROUND

The act of hair conditioning is often referred to as a generic process of applying one or more products to the hair, separately or in a mixture. The desired effect of applying a hair conditioning product is to alter the frictional and/or mechanical properties of the hair.

Hair conditioning materials can be applied to the hair when the hair is wet, for example during showering, or when the hair is dry. Most commonly, the term refers to the former. Hair conditioning materials are usually applied from a formulation comprising the conditioning materials in conjunction with a number of lipophilic ingredients.

Conditioning materials generally fall in to two main categories. Those that have alkyl chains with a cationically charged group (or a group able to carry a cationic charge) at one end and those that are non-ionic, hydrophobic, high molecular weight materials (usually polymers) based on silicone.

Although the term "conditioning" is used generically to describe the effect above, the processes of and materials required to achieve this effect are different depending on whether the hair is wet or dry.

When the conditioning formulation is applied to wet hair, the reduction of friction between the fibres is believed to be due to the conditioning materials forming a hydrophobic coating on the hair and repelling water.

For the cationic materials described above, the hydrophobic coating is produced when the cationic charge attaches to the naturally anionic surface of the hair and the lipophilic chain orientates outwards. A boundary is set up between the lipophilic chain and the water. Due to the immiscibility of these layers, this boundary has low friction.

For the non-ionic hydrophobic silicone materials, the large molecular weight enables the material to coat the hair. The hydrophobicity of the material causes it to be substantive to the hair rather than being removed by any aqueous media. The boundary mechanism for friction reduction is believed to be the same in this case, although the silicone layer may have inherent lubrication properties due to its chemical structure and physical properties.

Relatively, a consumer of hair condition products would spend a greater proportion of time with dry hair than with wet hair. Therefore the materials used should ideally also have a conditioning effect once the hair is dry.

The removal of water during the drying process removes the boundary lubrication that gives the friction reduction in the wet state. On dry hair, the lipophilic coating provides a level of lubrication between fibres but in this case the mechanism is different depending on the chemistry of the material chosen.

For the cationic materials, although the surface of the hair is essentially modified to become lipophilic, the lipophilic chains are ionically bound to the hair and their structure and physical properties do not allow for a flowable, slippery surface so the level of friction reduction is limited. For the non-ionic hydrophobic silicones, the ability for the material to spread and form layers allows for "slip" over the surface even without the presence of water. This is as a result of the chemistry and physical properties of these silicone compounds.

However, due to the increasing requirement in recent years for cosmetic treatments, especially hair care formulations, to be free from silicone based materials there exists a need to provide comparable levels of conditioning on dry hair without the use of silicones, which is not achieved through the use of cationic conditioning materials.

SUMMARY OF THE INVENTION

We have surprisingly discovered a hair care formulation and use thereof which overcomes or significantly reduces at least one of the aforementioned problems.

Accordingly, the present invention provides the use of a diester of a C8-C26 Guerbet alcohol and a C4-C40 dicarboxylic acid as an active ingredient in a hair care formulation.

The invention further provides a hair care formulation comprising a diester of a C8-C26 Guerbet alcohol and a C4-C40 dicarboxylic acid.

The invention yet further provides method of conditioning hair which comprises applying a hair care formulation comprising a diester of a C8-C26 Guerbet alcohol and a C4-C40 dicarboxylic acid to hair, and optionally rinsing the hair.

The invention also provides a pre-emulsion comprising a diester of a C8-C26 Guerbet alcohol and a C4-C40 dicarboxylic acid, and water.

By the use of the term Guerbet alcohol, we mean an alcohol which is formed by the Guerbet reaction. The Guerbet reaction is an organic reaction converting a primary aliphatic alcohol into its β-alkylated dimer alcohol with the loss of one equivalent of water. Guerbet alcohols are branched, and essentially saturated alcohols.

The Guerbet alcohol is preferably a C12 to C24 alcohol, more preferably a C14 to C22 alcohol and most preferably, a C16 to C20 alcohol. Especially preferred Guerbet alcohols include hexyl decyl alcohol, octyl decyl alcohol and octyl dodecyl alcohol.

There are various Guerbet alcohols on the market, e.g. Eutanol G/G16 (C16-C20 Guerbets) from BASF Personal Care and Nutrition GmbH. Sasol has various Isofol grades on the market (e.g. Isofol C12 to C32). Exxon has various Exxal C16 to C26 grades on the market, and Jarchem Industries supplies e.g. the Jarcol C12 to C36 grades. Evonik Goldschmidt GmbH supplies e.g. Tegosoft G 20.

The dicarboxylic acid starting material may be linear or branched, saturated or unsaturated, and aliphatic or aromatic.

In one embodiment, the dicarboxylic acid is preferably a linear, more preferably saturated, dicarboxylic acid. Preferably, the linear, more preferably saturated, dicarboxylic acid has a carbon chain length of between C4 and C22, more preferably between C6 and C20, more preferably between C8 and C18, and most preferably between C8 and C14.

The dicarboxylic acid may be represented by the formula HOOC—R—COOH. R can be saturated or unsaturated, linear or branched and can be aromatic e.g. a phenyl ring (thus giving a phthalic, terephthalic or iso-phthalic dicarboxylic acid), or and desirably aliphatic, typically an alkylene or alkenylene group which may also comprise an alkoxy, e.g. ethoxy and/or propoxy, group, and may be linear or branched, and may be cyclic though it is desirably open chain. Commonly R is a group —$(CH_2)_n$—, where n is from 2 to 20, usually from 6 to 16 and particularly from 6 to 12. Because mixtures of different dicarboxylic acids (or reactive derivatives) may be used, n may be non-integral, because it can be an average. The group R is usually unsubstituted, but may be substituted e.g. with hydroxyl and/or carboxyl groups, as in malic acid (which has a hydroxyl) or citric acid (which has both). Preferred dicarboxylic acids include C8, C9, C12 and C18 dicarboxylic acids. Especially preferred dicarboxylic acids include C9 and C12 dicarboxylic acids.

In an alternative embodiment, the dicarboxylic acid comprises a dimer acid. By the term dimer acid, we mean the dimeric oligomerisation products derived from unsaturated fatty acids, principally C18 unsaturated acids.

The dimer dicarboxylic acid used as a starting material herein is or includes residues based on fatty acid dimer residues. Fatty acid dimers (commonly referred to simply as "dimer acids") are the well-known, mainly dimeric, oligomerisation products derived from unsaturated fatty acids (industrially principally oleic, linoleic and/or linolenic acids), typically thermally polymerised, usually using acid catalysts e.g. acidic sites on clay. Generally they have average molecular weights corresponding to approximately two molecules of the starting fatty acid, so dimerised oleic acid has an average molecular weight corresponding to a nominally $C_{36}$ diacid, though commercial grades will typically also include $C_{18}$ ("monomer") and $C_{54}$ ("trimer") components. Generally the proportion of (i) residues of monomer will not be more than about 5 mol %, more usually not more than about 3 mol %, and desirably not more than about 2 mol %, of the total dimer acid used, and/or (ii) residues of trimer may be up to about 30 mol %, more usually from 1 to 25 mol %, and desirably from 2 to 20 mol %, of the total dimer acid residues used.

As manufactured, dimer acids have unsaturation but this may be reduced by hydrogenation. Hydrogenated or non-hydrogenated dimer acids may be used herein.

Preferably, the diester defined herein is used as a hair conditioning ingredient in a hair care formulation. Preferably, the diester is used as a hair conditioning ingredient which reduces the friction of hair in its dry state after application to the hair in either its wet or dry state. By this is meant the frictional forces experienced between hair fibres in dry hair, or between hair fibres and other substrates such as combs or brushes, or fingers when the hair is touched.

The diester, when applied to either wet or dry, preferably wet, hair suitably results in a decrease (compared to untreated hair) in the forces measured (e.g. total work required) in a hair sample, or tress, in its dry state. The total work required for dry hair is preferably less than $5 \times 10^{-2}$, more preferably less than $4.5 \times 10^{-2}$, particularly in the range from $1 \times 10^{-2}$ to $4 \times 10^{-2}$ Joules, and especially in the dry friction test described herein.

In addition, the diester, when applied to either wet or dry, preferably wet, hair suitably results in a decrease (compared to untreated hair) in the forces measured (e.g. total work required) in a hair sample, or tress, in its wet state. The total work required for wet hair is preferably less than $5 \times 10^{-2}$, more preferably less than $4 \times 10^{-2}$, particularly in the range from $1 \times 10^{-2}$ to $3.5 \times 10^{-2}$ Joules, and especially in the wet combing test described herein.

In one embodiment, the use of the diester achieves a low force in both dry and wet hair, suitably such that the difference in the total work required between the dry friction test and the wet combing test described herein is preferably less than $2 \times 10^{-2}$, more preferably less than $1.5 \times 10^{-2}$, particularly less than $1 \times 10^{-2}$, and especially less than $0.8 \times 10^{-2}$ Joules. Conditioning is generally easier to achieve with wet rather than dry hair, and therefore the total work required is usually greater for the dry friction test than the wet combing test described herein.

In one embodiment, the combined amount of total work required when using the diester in both the dry friction test and wet combing test described herein is suitably less than $9.5 \times 10^{-2}$, preferably less than $8.5 \times 10^{-2}$, more preferably less than $8 \times 10^{-2}$, particularly less than $7.5 \times 10^{-2}$, and especially less than $7 \times 10^{-2}$ Joules.

The hair care formulation comprising the diester defined herein may be a hair cleansing, conditioning, de-tangling, colouring, colour-protecting or styling formulation. The hair care formulation is preferably a friction modifying formulation operable to reduce the surface friction of human or animal hair fibres, preferably wet or dry human or animal hair fibres, more preferably dry human or animal hair fibres.

Preferably, the diester used herein, when added to the hair care formulation is anhydrous. By the term anhydrous, it is meant that the compound preferably comprises a maximum of 10% by weight water. More preferably, the diester comprises a maximum of 7% by weight water, most preferably, 5% and desirably 2% by weight. Preferably, the diester comprises 0.01% to 10% by weight water, preferably 0.05% to 5%, most preferably 0.1% to 2% by weight.

The diester used in the present invention may be used alone, or if desired in combination with other active ingredients, especially other hair conditioning ingredients, particularly to ensure that the desired conditioning effect is achieved for a particular product.

Preferably, the diester is present in the hair care formulation at a concentration of up to 40% by weight based on the total weight of the formulation, preferably up to 30%, more preferably up to 25%, and most preferably up to 20% by weight.

Preferably, the diester is present in the hair care formulation at a concentration of at least 0.1% by weight based on the total weight of the formulation, preferably at least 0.5%, more preferably at least 0.8% and most preferably at least 1% by weight.

The hair care formulation may be of a rinse-off type, meaning that after application to the hair, the formulation is rinsed off; or a leave-on type, meaning that the formulation is left on the hair after application. For a rinse-off type formulation, the diester is preferably present at a concentration of between 0.1% and 10% by weight based on the total weight of the formulation, more preferably between 0.5% and 5% by weight, and most preferably between 0.8% and 3% by weight. For a leave-on type formulation, the diester is preferably present in the formulation at a concentration of between 1% and 40% by weight based on the total weight of the formulation, preferably between 2% and 30%, more preferably between 3% and 25%, and most preferably between 5% and 20% by weight.

In one embodiment of the invention, no further active conditioning ingredients are present in the hair care formulation. In this embodiment, the diester of a C8-C26 Guerbet alcohol and a C4-C40 dicarboxylic acid is the only active conditioning ingredient present in the formulation. Preferably, the formulation is free from additional conditioning components, for example quaternised materials or silicones. In this embodiment, the hair care formulation comprises at least one conditioning active consisting essentially of, or consisting of, the diester defined herein.

In an alternative embodiment, the diester is present in the hair care formulation in combination with at least one other additional hair conditioning ingredient. When used with additional hair conditioning ingredients, the proportion of diester in the hair care formulation will generally be from 25% to 95%, more usually from 40% to 80%, by weight of the total hair conditioning ingredients used. The total concentration of hair conditioning ingredients present in formulations when mixtures are used will be generally within the ranges given above for the diesters.

Examples of suitable additional hair conditioning ingredients include silicones, such as, but not limited to, dimethicone, cyclopentasiloxane and dimethiconol, as well as for shampoos: polyquaternium 10, polyquaternium 11, glycol distearate, guar hydroxypropyltrimonium chloride, panthenol; for conditioners: cetyl alcohol/cetearyl alcohol, behentrimonium chloride, stearamidopropyl dimethylamine, cetrimonium chloride, behentrimonium methosulphate; for hair oils: coconut oil, mineral oil, argan oil, jojoba oil, caprylic/capric triglycerides; and for styling products: cetearyl alcohol, PVP, panthenol, hydrolysed keratin.

Any additional hair conditioning ingredient used is preferably not silicone, i.e. the hair care formulation is preferably silicone-free, in particular is free of dimethicone, cyclopentasiloxane and/or dimethiconol.

The hair care formulation may also comprise additional components, for example, additional emollients, carriers, surfactants and the like.

Preferably, the hair care formulation further comprises a base vehicle to carry the diester. The base vehicle may be water and/or oil based depending on the intended end use of the formulation. In one embodiment, e.g. for a shampoo, the vehicle comprises a relatively high concentration of water. In this embodiment, water is suitably present in the hair care formulation at a concentration of at least 20% w/w, preferably at least 25% w/w, more preferably at least 28% w/w, and most preferably at least 30% w/w of the total formulation. Preferably, water is present in the hair care formulation at a concentration of up to 99.9% w/w, preferably up to 99% w/w, preferably, up to 98% w/w and most preferably up to 97% w/w of the total formulation.

In an alternative embodiment, the base vehicle is oil-based. In this embodiment, preferably, the base oil is mineral oil, coconut oil, argan oil, jojoba oil, olive oil, vegetable oil, sunflower oil. Synthetic esters such as PPG-3 benzyl ether myristate could also be used. A wide range of other synthetic esters may be used.

In this embodiment, preferably the base oil is present in the hair care formulation at a concentration of at least 20% w/w, preferably at least 25% w/w, more preferably at least 28% w/w, and most preferably at least 30% w/w of the total formulation.

Preferably, the base oil is present in the hair care formulation at a concentration of up to 99.9% w/w, preferably up to 99% w/w, preferably, up to 98% w/w, and most preferably up to 97% w/w of the total formulation.

Preferably, the hair care formulation further comprises an emulsifier. The emulsifier may be a non-ionic or cationic surfactant. The emulsifier may be naturally derived. Examples of suitable non-ionic emulsifiers include ethoxylated sorbitan esters, ethoxylated glyceryl esters, ethoxylated fatty alcohols (including lanolin alcohols), ethoxylated fatty acids (including lanolin fatty acids), glycerol fatty acid mono-esters, glycol fatty acid mono and di-esters, sugar esters (fatty acid mono and di esters of sucrose), fatty acid polyol (polyethylene glycol) esters and fatty alcohols (which may also act as co-emulsifiers). Examples of suitable cationic emulsifiers include cetrimonium chloride, behentrimonium chloride and behentrimonium methosulphate.

When present in the hair care formulation, the emulsifier is preferably present at a concentration of at least 0.2% w/w, preferably at least 0.5% w/w, more preferably at least 0.9% w/w, and most preferably at least 1.1% w/w based on the total weight of the formulation. Preferably, the emulsifier is present in the formulation at a concentration of up to 20% w/w, preferably up to 12% w/w, more preferably up to 7% w/w, and most preferably up to 5% w/w based on the total weight of the formulation. The concentration of emulsifier present is preferably higher than that present in a formulation of the same type comprising quaternised materials. This is to compensate for the absence of quaternised materials in the formulation which would usually have an emulsifying effect on the formulation.

The hair care formulation may further comprise at least one co-emulsifier. Preferably, the or each co-emulsifier is a viscosity modifier, able to modify the viscosity of the formulation, more preferably a viscosity builder, able to increase the viscosity of the formulation. Preferably, the or each co-emulsifier is a fatty alcohol, preferably a $C_{12}$ to $C_{20}$ alcohol, more preferably a $C_{16}$ to $C_{18}$ alcohol, or a mixture thereof. Suitable alcohols for use as co-emulsifiers in the hair care formulation include cetyl alcohol, stearyl alcohol and cetearyl alcohol.

The formulations according to the present invention, particularly a hair conditioner, may also contain other additional emollient materials, preferably emollient oils. Preferably, the emollient oil is a non-polar oil. Examples of emollient oils which are suitable for use in the present formulation include mineral or paraffin oil; esters of fatty acids and fatty alcohols, preferably $C_{10}$-$C_{20}$ acids or alcohols, although isopropyl esters may be used; fatty acid glycol esters; fatty acid triglycerides; esters and diesters of alkoxylated fatty alcohols; botanical (plant) extracts; and hydrocarbons, preferably $C_{12}$-$C_{16}$. Preferably, the emollient is mineral oil. When present in the formulation, the or each additional emollient is preferably present at a concentration of at least 1% and up to 30% by weight based on the total weight of the formulation.

The hair care formulation according to the present invention, particularly a shampoo, may also contain one or more other surfactants, for example sodium lauryl ether sulphate or cocamidopropyl betaine. When present in the formulation, the or each surfactant is preferably present at a concentration of between 1% and 20%, preferably between 2% and 15%, and more preferably between 4% and 10% by weight based on the total weight of the formulation.

The hair care formulation according to the present invention may also contain one or more proteins or derivatised proteins. When present in the formulation, the or each protein or derivatised protein is preferably present at a concentration of between 0.1% and 10%, preferably between 0.5% and 8%, and more preferably between 1% and 5% by weight based on the total weight of the formulation.

The hair care formulation according to the present invention may also contain one or more cationic ingredients. When present in the formulation, the or each cationic ingredient is preferably present at a concentration of between 0.01% and 10%, preferably between 0.05% and 8%, and more preferably between 0.1% and 5% by weight based on the total weight of the formulation.

The hair care formulation according to the present invention may also contain one or more silicones. When present in the formulation, the or each silicone is preferably present at a concentration of between 0.05% and 10%, preferably between 0.1% and 8%, and more preferably between 0.5% and 5% by weight based on the total weight of the formulation.

The hair care formulation according to the present invention may also contain one or more film forming components. When present in the formulation, the or each film forming component is preferably present at a concentration of between 0.01% and 5%, preferably between 0.05% and 3%, and more preferably between 0.1% and 2% by weight based on the total weight of the formulation.

Preferably, a hair conditioner formulation is acidic. Preferably the hair conditioner formulation has a pH of between 1 and 6, preferably between 2 and 5.5, more preferably of between 3 and 5, and most preferably of between 4 and 4.5.

The hair care formulations of the type defined herein may be in the form of aqueous compositions; oil in water emulsions; water in oil emulsions; anhydrous formulations, including massage oils, hair sprays/serums; detergent formulations; more particularly in personal care emulsion formulations such as oil in water emulsions and detergent formulations. Hair care emulsion formulations can take the form of pastes, creams, liquids and milks desirably, and aim to provide a pleasant aesthetic feel to the hair as well as improving manageability and visual appearance.

The hair care formulation may have a range of different consistencies and/or viscosities depending on the desired end use of the formulation.

When the hair care formulation has the viscosity of a conditioner, for example a cream emulsion, preferably a dropping consistency cream emulsion, the viscosity of the formulation is preferably at least 4000 Pa·s, preferably at least 5000 Pa·s, more preferably at least 6000 Pa·s and most preferably at least 8000 Pa·s at 25° C. and 1 atmosphere pressure. Preferably in this case, the viscosity of the formulation is up to 80,000 Pa·s, preferably up to 50,000 Pa·s, more preferably up to 25,000 Pa·s and most preferably up to 10,000 Pa·s at 25° C. and 1 atmosphere pressure.

When the hair care formulation has the viscosity of a shampoo for example, the viscosity of the formulation is preferably at least 500 cps, preferably at least 800 cps, more preferably at least 1000 cps and most preferably at least 1500 cps at 25° C. and 1 atmosphere pressure. Preferably in this case, the viscosity of the formulation is up to 10000 cps, preferably up to 8000 cps, more preferably up to 5000 cps and most preferably up to 4000 cps at 25° C. and 1 atmosphere pressure.

When the hair care formulation has the viscosity of a serum for example, the viscosity of the formulation is preferably at least 300 cps, preferably at least 500 cps, more preferably at least 800 cps and most preferably at least 1000 cps at 25° C. and 1 atmosphere pressure. Preferably in this case, the viscosity of the formulation is up to 10000 cps, preferably up to 8000 cps, more preferably up to 5000 cps and most preferably up to 3000 cps at 25° C. and 1 atmosphere pressure.

When the hair care formulation has the viscosity of an oil for example, the viscosity of the formulation is preferably at least 30 cps, preferably at least 50 cps, more preferably at least 80 cps and most preferably at least 100 cps at 25° C. and 1 atmosphere pressure. Preferably in this case, the viscosity of the formulation is up to 1000 cps, preferably up to 500 cps, more preferably up to 400 cps and most preferably up to 300 cps at 25° C. and 1 atmosphere pressure.

When the hair care formulation has the viscosity of a hair spray for example, the viscosity of the formulation is preferably at least 1 cps, preferably at least 5 cps, more preferably at least 8 cps and most preferably at least 1 cps at 25° C. and 1 atmosphere pressure. Preferably in this case, the viscosity of the formulation is up to 500 cps, preferably up to 400 cps, more preferably up to 300 cps and most preferably up to 200 cps at 25° C. and 1 atmosphere pressure.

The diester defined herein may be used to form a pre-emulsion which may be directly incorporated into an end use hair care formulation. The pre-emulsion may be an oil in water emulsion or a water in oil emulsion.

Preferably, the pre-emulsion comprises up to 60% by weight water based on the total weight of the pre-emulsion, preferably up to 50% water, more preferably up to 45% water, and most preferably up to 40% water.

Suitably, the pre-emulsion comprises up to 65% by weight diester defined herein based on the total weight of the pre-emulsion, preferably up to 60% diester, more preferably up to 55% diester, and most preferably up to 50% diester.

Preferably, the pre-emulsion further comprises an emulsifier. Either non-ionic or cationic emulsifiers may be used, including but not limited to ethoxylated fatty alcohols (laureth-x, steareth-x, C11-13 pareth-x, C11-15 pareth-x, oleth-x) where x=number of moles of Ethylene oxide from 2-100. Cationic emulsifiers include, but are not limited to cetrimonium chloride, behentrimonium chloride and behentrimonium methosulphate.

The emulsifier is preferably present in the pre-emulsion at a concentration of at least 0.2% w/w, preferably at least 0.5% w/w, more preferably at least 0.9% w/w, and most preferably at least 1.1% w/w, based on the total weight of the pre-emulsion. Preferably, the emulsifier is present in the pre-emulsion at a concentration of up to 20% w/w, preferably up to 12% w/w, more preferably up to 7% w/w, and most preferably up to 5% w/w, based on the total weight of the pre-emulsion.

The end use applications of such hair care formulations include hair conditioners, hair relaxer formulations, hair shampoos, hair styling products, leave-on hair products, water-free products, 2-in-1 foaming emulsions, emulsifier free products, mild formulations, silicone-free formulations, pigment containing products, sprayable emulsions, colour cosmetics and shower products.

Hair care formulations comprising the diester defined herein may include various other hair care ingredients. For example, suitable other ingredients include one or more ingredients such as cleansing agents, skin conditioning agents, hair styling agents, antidandruff agents, hair growth promoters, perfumes, sunscreen compounds, pigments, moisturizers, film formers, alpha-hydroxy acids, hair colours, detergents, thickening agents, antiseptic agents and surfactants.

Any or all of the disclosed features, and/or any or all of the steps of any method or process described, may be combined in any combination.

Each feature disclosed herein may be replaced by alternative features serving the same, equivalent or similar purpose. Therefore, each feature disclosed is one example only of a generic series of equivalent or similar features.

The above statements apply unless expressly stated otherwise.

The present invention will now be described further, for illustrative purposes only, in the following examples. All parts and percentages are given by weight unless otherwise stated.

The following test methods were used for wet combing and dry friction assessment. Materials were applied based on the idea of standardising the amount of water (and test diester) on the hair. This significantly reduces the error caused by varying water levels and substantivities of different materials. Although the test described is a 'leave-on' test, a 1,000 ppm dosage level was chosen to mimic the average quantity of material expected to be left on the hair after rinsing out a conditioning treatment.

(i) An initial test was conducted to quantify the mass of water a hair tress could retain in order to standardise the dosing for the testing of formulations containing the diester conditioning actives.

Water was applied to a dry European brown hair tress weighing 3 g, measuring 25 cm in length (ex Higo Royer, UK) using a micro-pipette at 200 mg increments and rubbed in with finger and thumb (wearing a nitrile glove). This process was repeated until the tress was saturated, i.e. by applying sufficient water to the hair so that, once the applied water had been rubbed in, no water droplet formed at the bottom of the tress after squeezing between finger and thumb. Results showed that an average of 1,600 mg of water applied to each tress and rubbed in achieved the desired level.

(ii) Calculations were made to work out the concentration of diester conditioning active required in the formulation to achieve the desired dosage level when 1,600 mg of the formulation was applied to the hair. For 1,000 ppm treatment level, 3 mg of diester was required for 3 g of hair. The diester was made up in a concentrated emulsion containing 60% diester. This was diluted with water to 0.3125% so that 1,600 mg of the diluted formulation (applied to a hair tress) contained 3 mg of diester.

(iii) A wet combing test using a Diastron MTT175 (Diastron Ltd) was performed. Each test was performed on 3 hair tresses. An average of 5 measurements were taken for each hair tress, and average values for the 3 hair tresses calculated.

(iv) The hair tresses were then dried overnight under controlled temperature and humidity conditions (21+/−1° C., 50+/−5% RH) and a dry friction (smoothness) test was performed on the dry hair, again using a Diastron MTT175, but this time set up using the parallelogram friction test apparatus with a normal force of 400 g being applied to the test probe.

EXAMPLE 1

Dioctyldodecyl dodecanedioate was produced by reacting commercially available 2-octyldodecanol (606 g, 2.0 mol) and dodecanedioic acid (230 g, 1.0 mol) in a suitable reaction vessel by heating, with stirring under a nitrogen atmosphere, to a temperature high enough to effect esterification (>100° C.). Reaction progress was monitored by the decline in acid value, with reaction deemed complete when the acid value was <5 mgKOH/g. If required, the rate of reaction can be increased by use of a suitable esterification catalyst* and/or application of vacuum. The resultant crude ester can be utilised as is or may be refined with suitable post-treatments (e.g. steam-stripping, distillation, water-washing, earth treatment, etc.).

*Examples include: p-toluenesulfonic acid, methanesulfonic acid, organotitanates, organotin compounds; inorganic acids such as sulphuric, orthophosphoric and hypophosphorous acids, zeolites and biological agents such as enzymes and microorganisms.

EXAMPLE 2

Dioctyldodecyl azelate was produced by reacting commercially available 2-octyldodecanol (144.1 g, 0.48 mol) and nonanedioic acid (45.0 g, 0.24 mol) using the general method described in Example 1.

EXAMPLE 3

The diesters produced in Examples 1 and 2, and a range of other diesters produced according to a similar synthetic method described in Examples 1 and 2, were subjected to the wet combing and dry friction tests described herein. The results are shown in Table 1.

TABLE 1

| Conditioning Active | Alcohol | Di-acid | Dry Friction (Joules) | Wet Combing (Joules) |
|---|---|---|---|---|
| None (Blank) | — | — | 5.98E−02 | 5.04E−02 |
| Dioctyldodecyl dodecanedioate | C20 | C12 | 3.83E−02 | 3.10E−02 |
| Dioctyldodecyl azelate | C20 | C9 | 4.10E−02 | 3.98E−02 |
| Dioctyldodecyl octadecanoate | C20 | C18 | 4.14E−02 | 3.01E−02 |
| Dioctyldecyl/hexyldecyl dodecanoate | C18/C16 | C12 | 4.40E−02 | 3.64E−02 |
| Dioctyldodecyl sebacate | C20 | C8 | 4.63E−02 | 4.71E−02 |
| Dihexyldecyl dodecanoate | C16 | C12 | 4.66E−02 | 3.74E−02 |

EXAMPLE 4

A blind experiment was conducted on hair tresses treated with either 1,000 ppm Silicone DC1785 (ex Dow Corning) (Comparative Example), or 1,000 ppm or 2,000 ppm dioctyldodecy dodecanedioate produced in Example 1. Tresses were ranked on a scale of 1 to 3 by 18 assessors in order of preference of smoothness. The results are shown in Table 2 below.

TABLE 2

| Assessor | Silicone DC1785 (1,000 ppm) (Comparative Example) | Dioctyldodecyl Dodecanedioate (1,000 ppm) | Dioctyldodecyl Dodecanedioate (2,000 ppm) |
|---|---|---|---|
| 1 | 3 | 1 | 2 |
| 2 | 3 | 2 | 1 |
| 3 | 2 | 1 | 3 |
| 4 | 1 | 2 | 3 |
| 5 | 1 | 2 | 3 |
| 6 | 2 | 1 | 3 |
| 7 | 3 | 2 | 1 |
| 8 | 1 | 3 | 2 |
| 9 | 2 | 3 | 1 |
| 10 | 2 | 3 | 1 |
| 11 | 1 | 3 | 2 |
| 12 | 1 | 3 | 2 |
| 13 | 1 | 3 | 2 |
| 14 | 1 | 2 | 2 |
| 15 | 1 | 1 | 1 |
| 16 | 2 | 1 | 3 |
| 17 | 1 | 3 | 2 |
| 18 | 3 | 1 | 2 |
| TOTAL | 31 | 37 | 36 |

The table value for the Friedman test using n=18 results is 6.333. The calculated test value in this experiment was 1.30. As the test value is below the table value, the results show no significant difference in smoothness between silicone treated hair tresses, or those treated with dioctyldodecyl dodecanedioate at either of the treatment levels tested.

EXAMPLE 5

A shampoo formulation was made of the following composition;

| Ingredients (INCI Name) | % w/w |
|---|---|
| Deionised water (Aqua) | to 100 |
| Crodateric ™ CAS 50 (Aqua (and) Cocamidopropyl Hydroxysultaine (ex Croda) | 10.0 |
| Arlasilk ™ EFA (Linoleamidopropyl PG-Dimonium Chloride Phosphate (and) Aqua (and) Propylene Glycol) (ex Croda) | 0.5 |
| Terraquat ™ BD (Bis-(Ethyl PPG-3 Behenate) Dimonium Methosulphate (and) Behenamidopropyl Dimethylamine) (ex Croda) | 1.5 |
| Crodafos ™ HCE (Oleth-5 Phosphate (and) Dioleyl Phosphate) (ex Croda) | 1.0 |
| Dioctyldodecyl Dodecanedioate (produced in Example 1) | 2.5 |
| Sodium Benzoate | 0.25 |
| Sodium Citrate | 0.25 |
| Disodium EDTA | 0.2 |
| Sodium Lauryl Sulphate | 10.0 |
| Sodium Laureth Sulphate | 20.0 |
| Ethylene Glycol Distearate | 0.5 |
| Preservative | qs |
| Fragrance | qs |

In normal use, the shampoo results in conditioning of both wet and dry hair.

EXAMPLE 6

A rinse-off conditioner formulation was made of the following composition;

| Ingredients (INCI Name) | % w/w |
|---|---|
| Part A | |
| Crodazosoft ™ DBQ (Quaternium-91 (and) Cetrimonium Methosulfate (and) Cetearyl Alcohol) (ex Croda) | 2.25 |
| Crodacol ™ CS90 (Cetearyl Alcohol) (ex Croda) | 2.0 |
| Crodacol ™ C90 (Cetyl Alcohol) (ex Croda) | 0.5 |
| Super Sterol Ester ™ ($C_{10}$-$C_{30}$ Cholesterol/Lanosterol Esters) (ex Croda) | 1.0 |
| Dioctyldodecyl Dodecanedioate (produced in Example 1) | 4.5 |
| Crodacel ™ QS (PG-Hydroxyethyl Cellulose Steardimonium Chloride) (ex Croda) | 0.2 |
| Deionized Water | 85.25 |
| Part B | |
| Crosilk ™ 10,000 (Hydrolyzed Silk) (ex Croda) | 1.0 |
| Hydrotriticum ™ 2000 (Hydrolyzed Wheat Protein) (ex Croda) | 1.0 |
| Keravis ™ (Hydrolyzed Vegetable Protein PG-Propyl Silantriol) (ex Croda) | 1.0 |
| Crodarom Phytexcell Green Tea ™ (Glycerin (and) Butylene Glycol (and) Water (and) *Camellia Sinensis* Leaf Extract) (ex Croda) | 0.15 |
| Crodarom Phytexcell Chamomile ™ (Glycerin (and) Butylene Glycol (and) Water (and) *Chamomilla Recutita Matricaria*) Extract) (ex Croda) | 0.15 |
| Part C | |
| Phenova (Phenoxyethanol (and) Methyl Paraben (and) Ethyl Paraben (and) Butyl Paraben (and) Propyl Paraben (and) Isobutylparaben) | 1.0 |

| Ingredients (INCI Name) | % w/w |
|---|---|
| pH: 4.5 Viscosity: 11,200 cps (RVT Spindle TC @ 10 RPM @ RT) | |

Procedure: The components of Part A were combined, heated to 75°-80° C., and allowed to cool to 40° C. The components of Part B were added individually. Part C was added, and the pH adjusted to 4.5 with triethylamine.

In normal use, the rinse-off conditioner results in conditioning of both wet and dry hair.

EXAMPLE 7

A silicone-free hair oil formulation was made of the following composition;

| Product (INCI Name) | Functionality | % w/w |
|---|---|---|
| Crodamol ™ STS (PPG-3 Benzyl ether myristate) (ex Croda) | Base oil | to 100 |
| Dioctyldodecyl Dodecanedioate (produced in Example 1) | Conditioning | 20.0 |
| Crodamol ™ GTCC (Caprylic/Capric triglycerides) (ex Croda) | Light Emollient | 5.0 |
| Crodamol ™ CAP (Cetearyl Ethylhexanoate (and) Isopropyl Myristate) (ex Croda) | Hair gloss | 5.0 |
| Jojoba Oil (*Buxus Chinensis*) (ex Croda) | Plant extract | 1.0 |
| BHT | Anti-oxidant | 0.05 |

Procedure: All the components were added together and mixed until homogenous.

In normal use, the silicone-free hair oil formulation results in conditioning of both wet and dry hair.

The above examples illustrate the improved properties of the hair care formulation and use thereof according to the present invention.

The invention claimed is:

1. A hair care formulation comprising a diester of a C8-C26 Guerbet alcohol and a C4-C40 dicarboxylic acid and at least one additional hair care ingredient.

2. The hair care formulation of claim 1 which is silicone-free.

3. A method of conditioning hair which comprises applying a hair care formulation comprising a diester of a C8-C26 Guerbet alcohol and a C4-C40 dicarboxylic acid to hair, and optionally rinsing the hair.

4. The method according to claim 3 wherein the diester is a hair conditioning agent.

5. The method according to claim 3, comprising applying the hair care formulation to dry hair.

6. The method according to claim 3, comprising applying the hair care formulation to wet hair.

7. The method according to claim 3 wherein the total work required for wet hair is less than $3.5 \times 10^{-2}$ Joules.

8. The method according to claim 3 wherein the combined amount of total work required for both dry hair and wet hair is less than $8 \times 10^{-2}$ Joules.

9. The method according to claim 3 wherein the hair care formulation is silicone-free.

10. The method according to claim 3 wherein the hair care formulation comprises a hair conditioning active consisting of at least one diester.

11. The method according to claim 3 wherein the diester comprises dioctyldodecyl dodecanedioate.

12. The method according to claim 3 wherein wherein the total work required for dry hair is less than $4.5 \times 10^{-2}$ Joules.

13. The method according to claim 3, wherein the C4-C40 dicarboxylic acid comprises a C12 or C18 dicarboxylic acid.

14. The method according to claim 3, wherein the C4-C40 dicarboxylic acid is a dimer acid.

15. A pre-emulsion consisting of a diester of a C8-C26 Guerbet alcohol and a C4-C40 dicarboxylic acid, and water, and optionally an emulsifier, wherein the diester is present in an amount of up to 65% by weight relative to the total weight of the pre-emulsion, the water is present in an amount up to 60% by weight relative to the total weight of the pre-emulsion, and the emulsifier, if present, is present in an amount up to 20% by weight relative to the total weight of the pre-emulsion.

* * * * *